(12) United States Patent
Brown et al.

(10) Patent No.: US 7,572,947 B2
(45) Date of Patent: Aug. 11, 2009

(54) OLIGOMERIZATION REACTION

(75) Inventors: Stephen Harold Brown, Bernardsville, NJ (US); Georges Marie Karel Mathys, Bierbeek (BE); Paul Hamilton, Brussels (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 328 days.

(21) Appl. No.: 11/500,004

(22) Filed: Aug. 7, 2006

(65) Prior Publication Data

US 2007/0191661 A1    Aug. 16, 2007

Related U.S. Application Data

(60) Provisional application No. 60/722,341, filed on Sep. 30, 2005.

(51) Int. Cl.
*C07C 2/12* (2006.01)
(52) U.S. Cl. .................. 585/533; 585/520; 585/532
(58) Field of Classification Search .......... 585/510, 585/511, 514, 517, 520, 532, 533
See application file for complete search history.

(56) References Cited

U.S. PATENT DOCUMENTS

| | | | | |
|---|---|---|---|---|
| 3,657,150 | A | 4/1972 | Juguin et al. | 252/435 |
| 4,587,368 | A | 5/1986 | Pratt | 585/12 |
| 5,134,242 | A | 7/1992 | Le et al. | 585/533 |
| 5,672,800 | A | 9/1997 | Mathys et al. | 585/520 |
| 5,811,608 | A | 9/1998 | Stine et al. | 585/316 |
| 5,895,830 | A | 4/1999 | Stine et al. | 585/259 |
| 6,072,093 | A | 6/2000 | O'Neill et al. | 585/514 |
| 6,143,942 | A | 11/2000 | Verrelst et al. | 585/533 |
| 6,403,853 | B1 | 6/2002 | Abrevaya et al. | 585/533 |
| 6,649,802 | B1 | 11/2003 | Frame et al. | 585/533 |
| 6,911,505 | B2 | 6/2005 | Small | 526/130 |
| 2005/0014630 | A1 | 1/2005 | Dakka et al. | 502/60 |

FOREIGN PATENT DOCUMENTS

| | | |
|---|---|---|
| WO | WO 95/22516 | 8/1995 |
| WO | WO 01/83407 | 11/2001 |
| WO | WO 03/082780 | 10/2003 |

*Primary Examiner*—In Suk Bullock
(74) *Attorney, Agent, or Firm*—Andrew B. Griffis

(57) ABSTRACT

The invention is directed to a method of selectively oligomerizing olefin monomers by controlling feedstock composition and reaction conditions. Reaction conditions are chosen to include at least one of: (a) dimer recycle; (b) staged injection of monomer; and (c) utilization of a two catalyst system.

15 Claims, No Drawings

OLIGOMERIZATION REACTION

CROSS REFERENCE TO RELATED APPLICATION

This application claims the benefit of Provisional Application No. 60/722,341 filed Sep. 30, 2005, the disclosure of which is incorporated by reference.

FIELD OF THE INVENTION

The invention relates to selective conversion of light olefins to heavier olefins, such as propylene to nonene.

BACKGROUND OF THE INVENTION

The oligomerization of light olefins (typically mixtures comprising propylene and butenes) to heavier olefins is important for the production of gasoline, distillate, and feedstock for other processes (e.g., C6 to C14 olefins converted in the Oxo Process, hereinafter "Oxo", to functionalized products such as aldehydes and alcohols). See, for instance, U.S. Pat. No. 3,657,150. Typical commercial processes employ multiple reactors filled with solid phosphoric acid catalyst (SPA catalyst).

For the production of distillate and feeds to Oxo, there is a need for trimer selective catalysts, e.g., conversion of propylene selectively to nonenes as Oxo feedstock, and conversion of butenes selectively to dodecenes for use as high quality, low sulfur diesel or jet fuel. Efforts to increase the yield of linear or near linear trimers using, for instance, zeolite catalysts, have not significantly solved the problem. See, for instance, WO 95/22516.

U.S. Pat. No. 4,587,368 uses the delayed addition of fresh monomer to improve the yield of tetramers and pentamers of alpha olefin monomers. Prior to delayed addition of monomer, the trimer yield is "in excess of 20% or even 25%, by total oligomer weight". After staged addition of monomer, the yield of trimer decreases.

A process for oligomerization of lower olefins in paraffin-containing mixed aliphatic feedstock to yield branched intermediate olefins is disclosed in U.S. Pat. No. 5,134,242. Selectivity of conversion of propylene to nonene as high as 62% is reported.

U.S. Pat. No. 5,811,608 teach the production of saturated oligomers wherein the saturation of the heavy olefins is improved by the recycle of the heavy paraffins to the oligomerization zone. The recycle is said to inhibit fouling of the oligomerization zone and improves selectivity to C8 isomers. See also U.S. Pat. No. 5,895,830.

U.S. Pat. No. 6,072,093 utilizes a recycle of cycloparaffins in a process for oligomerizing light olefins to heavier olefins. The recycle is said to extend the catalyst life.

U.S. Pat. No. 6,143,942 utilizes a two-catalyst system said to maximize the proportion of nonene resulting from the oligomerization of propene. The patent suggests that C3 monomers are converted to hexenes by one of the catalysts (ZSM-22) and the other catalyst (ZSM-5) converts hexenes to nonenes by reaction with propene. A selectivity as high as about 51% is observed.

The yield of nonene using a feed of predominantly propylene is said to be maximized by "optimizing the reaction conditions", according to U.S. Pat. No. 6,403,853. Selectivity of as high as 48% to nonene is exemplified.

Other references of interest include U.S. Pat. Nos. 5,672,800; 6,649,802; and 6,911,505.

The present inventors have surprisingly discovered that olefin monomers can be selectively oligomerized using zeolite catalysts by providing feedstock under suitable conditions to optimize the yield of trimers of said monomer.

SUMMARY OF THE INVENTION

According to the invention, the composition of feedstock in an oligomerization reaction is controlled to optimize selectivity of an oligomerized product.

In a preferred embodiment, the invention is directed to a method of selectively trimerizing monomers by controlling feedstock composition and reaction conditions.

In other preferred embodiments, feedstock composition is controlled by least one of: (a) recycle of intermediate or final product (e.g., dimer); (b) staged injection of reactant (e.g., monomer); and (c) utilization of at least two catalysts differing in oligomerization selectivity.

Combinations of the above-recited preferred embodiments are also preferred embodiments of the present invention.

It is an object of the invention to provide practical means of controlling oligomerization of olefin monomers by controlling feedstock composition.

It is another object of the invention to improve operating conditions by increasing the solvency of the reaction medium and more evenly spread heat release across the catalyst bed(s) in order to better control the oligomerization of light olefins to heavier olefins.

These and other objects, features, and advantages will become apparent as reference is made to the following detailed description, preferred embodiments, examples, and appended claims.

DETAILED DESCRIPTION

According to the invention, the composition of feedstock to one or more oligomerization catalysts are controlled to optimize selectivity of an oligomerization product.

In embodiments, the invention is directed to a method of selectively trimerizing monomers, particularly C3 and/or C4 monomers. In preferred embodiments the monomers are olefins derived from a thermal or catalytic cracking process and comprise C3 and/or C4 olefins.

In a preferred embodiment, selective trimerization of at least one monomer may is provided by a method comprising oligomerization of said at least one monomer in the presence of a high proportion of dimer of said monomer. By way of non-limiting examples, in preferred embodiments the composition of the feedstock is controlled so that propylene is oligomerized selectively to nonene in the presence of hexene, or butene is oligomerized selectively to dodecene in the presence of octene, or a mixture of C3 and C4 olefins can be selectively oligomerized to nonenes and dodecenes in the presence of hexenes and octenes.

While the amount of oligomer of the monomer of interest can be determined by one of ordinary skill in the art in possession of the present disclosure, typically the amount of the oligomer (e.g., dimer and trimer) will be on the order of twice that of the monomer, on a weight percent basis. A diluent such as a paraffin may also be present.

In a preferred embodiment, the composition comprises 10-40 wt % of the monomer of interest, 40-80 wt % of oligomers consisting of dimer and trimer (which may include from 0 wt % or 10 wt % or 20 wt % or 30 wt % or 40 wt % or 50 wt % up to about 70 wt % or 80 wt % or 90 wt % of trimer of said monomer), and, optionally, about 30 wt % or less, such as 10 wt % to about 25 wt % or 15 wt % to about 20 wt %, of other olefins. Non-reactive diluent (e.g., paraffin) may or may not be present, and when present may be in the amount of 1 wt % or 5 wt % or 10 wt % or 20 wt % or 30 wt % or 40 wt % up to about 50 wt % or 60 wt % or 70 wt %. The aforementioned ranges are particularly preferable when the monomer of interest is propylene.

For instance, in a preferred embodiment, trimerization of propylene to nonene occurs by contacting a feedstream with an oligomerization catalyst, such as ZSM-57 (IUPAC nomenclature="MFS") with a feedstock comprising 10-40 wt % propylene, 40-80% hexene and nonene, and <30% other olefins.

The "other olefins" may be, for instance in the embodiment discussed immediately above, butenes. Butenes may include all possible isomers of butene. Butenes are a preferred type of "other olefins". Oligomers of butenes, particularly octenes, are also a preferred "other olefins". Numerous different "other olefins" may also be present, including, without limitation, 3-methyl-pentene-1/-2, 3-methyl-hexene-1/-2, 3-ethyl-pentene-1/-2, 2-methyl-pentene-1/-2, 2-methyl-hexene-1/-2, 2-ethyl-pentene-1/-2, and the like, particularly where the "other olefins" are present as a result of recycle, discussed below.

In another preferred embodiment, the "monomer" of interest may comprise a mixture, e.g., both propylene and butenes, and thus in a still more preferred embodiment trimerization of propylene and butenes to a mixture of C9-C12 occurs by contacting a feedstream with an oligomerization catalyst, such as ZSM-57, with a feedstock comprising 10-40 wt % propylene and butenes, 40-80% hexene, heptene, octene, nonene, decene, undecene, and dodecene, and <30% other olefins.

In addition to providing an initial feed having the appropriate amounts of monomer and dimer, other practical methods of controlling feedstock composition and reaction conditions include: (a) recycle of intermediate or final product (e.g., dimer); (b) staged injection of reactant (e.g., monomer); and (c) utilization of at least two catalysts differing in oligomerization selectivity monomer.

Thus, in one preferred method, intermediate product, e.g., dimers, may be recycled so that oligomerization of monomers occurs in the presence of a high proportion of oligomers of the monomer. The recycle may include trimers and other olefins and typically may simply be recycle of a portion of the product in a continuous process or a portion or all of the product in a batch process, or dimers (or higher order oligomers and/or other olefins may be provided from some other process or may be purchased).

Examples of recycle of intermediate or final product are per se well-known in the art. Recycle per se is taught, for instance, in the above-mentioned U.S. Pat. Nos. 5,811,608 and 6,072, 093. At least one of the present inventors has recently described apparatus optionally using a piping system allowing for recycle in U.S. patent application Ser. Nos. 11/140, 153, filed May 31, 2005, and 11/209,942, filed Aug. 23, 2005.

In another preferred embodiment, dimers are selectively recycled so that oligomerization occurs in the presence of a high proportion of dimers of the olefin.

In an embodiment, in the case where the feed comprises propylene and butenes, a preferred recycle comprises heptenes, which may be separated from hexene product prior to recycling. In an alternative, the heptenes and hexenes may be separated to create a first recycle stream comprising predominantly hexenes and a second recycle stream comprising predominantly heptenes, and the two streams reacted separately.

The term "predominantly" as used herein means that the named species is present in amounts greater than any other species. In addition, a species such as "hexene" means all isomers of that species, unless otherwise specified.

In another method of controlling feedstock composition, at least two oligomerization reactors are arranged or piped in series and equipped with distributors to allow interstage injection of fresh monomer feed. Staged or "interstage" injection per se is also known in the art, such as disclosed in the aforementioned U.S. Pat. No. 4,587,368, as well as the aforementioned U.S. patent application Ser. No. 11/209,942, filed Aug. 23, 2005.

In still yet another preferred embodiment, at least two different catalysts are arranged in series, the first catalyst selective for dimerization of olefin monomers and the second catalyst selective for combining a olefin monomer with the olefin dimer of said monomer. The arrangement of catalysts may be by stacking one catalyst on top of another within a single reactor, by arranging or piping two catalyst beds in series, or a combination thereof.

The catalyst beds in series may be, for instance, at least two tubular reactors in series, at least two catalyst beds in series in a chamber reactor, or a combination of at least one tubular reactor and at least one chamber reactor.

The use of two or more catalysts in series has recently been described in both of the aforementioned U.S. Patent Applications and synergistic effects using dual catalysts have been noted previously in, for instance, U.S. Pat. Nos. 6,875,899; 6,770,791; and 6,143,942.

These preferred methods may be combined by, for instance staged injection of fresh monomer subsequent to a first reactor having a catalyst selective for dimerization, whereby the fresh monomer is reacted with an intermediate product, preferably dimer of said monomer, from said first reactor in a second reactor having a catalyst selective for oligomerization of said monomer and said dimer to yield trimer of said monomer, and/or by an arrangement of two catalyst beds in series having a recycle of part or all of product whereby interstage injection of the product between the first and second catalyst beds in series is provided for. By way of further example, both stacked bed and recycle can be used, e.g., in a preferred embodiment, a dimer-selective catalyst such as ZSM-22 (IUPAC nomenclature="TON") is stacked with ZSM-57 and hexene recycle is provided.

One of ordinary skill in the art in possession of the present disclosure can extrapolate the above examples to provide for numerous other products other than those specifically disclosed. For instance, taking the example of two reactors in series producing trimer, with interstage injection of fresh monomer to react with dimer in the second reactor, a third reactor may be provide with staged injection of fresh monomer prior to the third reactor, so as to react with trimer from the second reactor to produce tetramer selectively.

While the reaction conditions useful in the present invention are not narrowly defined, nevertheless there are preferred reactor conditions which, although not absolutely critical to achieving a preferred product (and without wishing to be bound by theory), provide one or more of improved catalyst stability, longer catalyst lifetime, higher proportion of less branched product molecules, tolerance to a higher proportion of heteroatom impurities in the feed, and superior reactor economics. Preferred operating temperatures are generally between 80° C. to 350° C. More typically the reaction temperature is in the range of about 130° C. to 320° C., such as 135° C. to 310° C. and for example 160° C. to 260° C. Preferably, the weight hourly space velocity ranges from $0.1h^{-1}$ to $20h^{-1}$ typically between $0.2\ h^{-1}$ to $10\ h^{-1}$. The pressure is conveniently ranging from about 28 barg to about 110 barg (about 2,860 kPa to about 11,000 kPa).

The present invention has been described generally above, with reference to certain embodiments. The following specific examples are provided as "representative" and, although they may describe preferred embodiments, are not intended to limit the invention.

Experimental

Pure feedstock components was purchased from Air Liquide and used as received. Diethylsulfide (DES) for sulfur spiking was purchased from Aldrich and used as received. Propylene oligomerization is carried out with a 50 wt % propylene/50 wt % paraffin synthetic feedstock. The catalyst, ZSM-57, is formed into extrudates. Analytical data is provided in Tables 1 and 2.

Micro-Unit Methods:

EXAMPLES 1-8

Operations conditions are typical for the ones used in olefin oligomerizations: 130-320° C., and 70 barg (7,000 kPa).

All experiments were conducted in pilot tubular reactors having multiple parallel tubes, the reactors designed to closely approximate commercial units but on a smaller scale. Feedstock is pumped from feed vessels using displacement pumps controlled by mass flow meters. The feed is saturated with water by passing upwards through a vessel containing water at a constant 40° C. temperature. After exiting the hydrator the feed is pre-heated to the heater temperature and then runs downwards through a fixed-bed reactor equipped with an internal thermowell. The oligomerization reaction is exothermic leading to a non-isothermal temperature profile down the length of the catalyst bed.

No $C_2$-gasses are fed or produced, and there is no evidence of any feedstock cracking. The product is cooled to near room temperature and depressured to 20 bar (2,000 kPa). Total reactor effluent samples are taken at 20 bar. After flowing through the sample vessels, the effluent is depressured from 20 barg to atmospheric. Unreacted feedstock olefins and paraffins escape out the vent.

The total reactor effluent is analyzed by GC. The feed and product olefin/paraffin ratios are compared in order to measure conversion. Liquid product is analyzed on a GC after hydrogenation of the product olefins to paraffins. Carbon number distribution and isomer distribution is determined on the hydrogenated liquid product.

Results:

EXAMPLE 1

Samples 1-8

Feedstock contacted catalyst to convert propylene to oligomers under conditions specified (70 bar pressure, 2 weight hourly space velocity (WHSV), and 222° C.). Feedstock composition, conditions, and product selectivity information are provided in Table 1. The feedstock contained 20 ppm DES added to simulate impurities in the feedstock.

EXAMPLE 2

Samples 9-16

The above experiments were repeated under nearly identical conditions (70 bar pressure, WHSV=2, and 226° C.) except feedstock composition. The feedstock contained 12 ppm DES added to simulate impurities in the feedstock.

TABLE 1

| | Conditions and Products from Example 1 | | | | | | | |
|---|---|---|---|---|---|---|---|---|
| | sample | | | | | | | |
| | 1 | 2 | 3 | 4 | 5 | 6 | 7 | 8 |
| Temp ° C. | 222 | 222 | 222 | 222 | 222 | 222 | 222 | 222 |
| WHSV | 2 | 2 | 2 | 2 | 2 | 2 | 2 | 2 |
| Feed (wt %) | | | | | | | | |
| propane | 12 | 12 | 12 | 12 | 12 | 12 | 12 | 12 |
| propylene | 50 | 50 | 50 | 50 | 50 | 50 | 50 | 50 |
| butanes | 38 | 38 | 38 | 38 | 38 | 38 | 38 | 38 |
| hexenes | 0 | 0 | 0 | 0 | 0 | 0 | 0 | 0 |
| higher olefins | 0 | 0 | 0 | 0 | 0 | 0 | 0 | 0 |
| Product Data* | | | | | | | | |
| Conv % | 89.9 | 97.2 | 97.7 | 97.6 | 94.6 | 91.7 | 91.4 | 85.8 |
| Hexenes | 9.2 | 5.0 | 5.0 | 5.5 | 7.2 | 8.9 | 8.5 | 11.1 |
| Nonenes | 54.1 | 49.5 | 48.9 | 49.9 | 53.1 | 54.8 | 55.5 | 55.5 |
| heavies + cracking | 24.5 | 32.0 | 32.6 | 31.7 | 27.4 | 24.6 | 24.3 | 22.5 |
| nonenes/C7+ | 0.60 | 0.52 | 0.51 | 0.53 | 0.57 | 0.60 | 0.61 | 0.62 |

*results for "Product Data" in both Tables 1 and 2 are in weight percent based on all olefins in the product stream, except: "conv %" is the percent of monomer (propylene) oligomerized; "nonenes/C7+" is the ratio of desired trimer product to C7+ olefin species (heptene, octene, etc.).

TABLE 2

Conditions and Products from Example 2

| | sample | | | | | | | |
|---|---|---|---|---|---|---|---|---|
| | 9 | 10 | 11 | 12 | 13 | 14 | 15 | 16 |
| Temp ° C. | 226 | 226 | 226 | 226 | 226 | 226 | 226 | 226 |
| WHSV | 9 | 9 | 9 | 9 | 9 | 9 | 9 | 9 |
| Feed (wt %) | | | | | | | | |
| propane | 20 | 20 | 20 | 20 | 20 | 20 | 20 | 20 |
| propylene | 13 | 14 | 16 | 16 | 17 | 18 | 20 | 21 |
| butanes | 10 | 10 | 10 | 10 | 10 | 10 | 10 | 10 |
| hexenes + nonenes | 47 | 47 | 47 | 47 | 46 | 46 | 44 | 44 |
| higher olefins | 10 | 9 | 7 | 7 | 7 | 6 | 6 | 5 |
| Product Data* | | | | | | | | |
| Conv % | 94.9 | 94.1 | 91.0 | 90.7 | 89.9 | 89.0 | 86.1 | 85.6 |
| hexenes | 22.7 | 24.0 | 25.6 | 26.9 | 27.7 | 27.0 | 30.7 | 28.8 |
| nonenes | 54.7 | 54.8 | 53.4 | 54.0 | 53.9 | 54.0 | 52.1 | 53.4 |
| heavies + cracking | 12.0 | 11.0 | 11.3 | 9.8 | 9.3 | 9.6 | 8.6 | 8.8 |
| nonenes/C7+ | 0.71 | 0.72 | 0.72 | 0.74 | 0.74 | 0.74 | 0.75 | 0.75 |

Example 1 shows that processing pure propylene feedstock over ZSM-57 catalyst at conditions representative of typical oligomerization unit operations leads to a product slate with 20-30 wt % C13+ (heavies) and cracked (C7, C8, C10, C11) products. Nonenes do not exceed 61 wt % of the C7+ product at any conversion above 90%. Example 2 shows that by changing the feedstock to within the range of the invention, nonene selectivity increases and the amount of heavies and cracked products is more than halved.

This surprising data suggests that the reaction of propylene with hexenes over zeolite catalyst proceeds via the expected stepwise mechanism, while the reaction of pure propylene is apparently not selective for hexenes but instead leads to the production of heavy and cracked products even at low conversion. In other words, the kinetic product is not exclusively hexenes as expected but includes heavy and cracked products. (Note that similar results were obtained on a sulfur-free feedstock.

Example 1 shows that selectivity at the industrially desirable temperature window between 190 and 280° C. is within the range of selectivities achieved by the prior art. One advantage of the present invention is to enable the attractive selectivities demonstrated at low temperatures to be maintained well in excess of 225° C., which is commercially-desirable because of inter alia higher throughput, while achieving significantly higher selectivities.

Note also that numerous prior art methods are concerned with lowering reaction temperatures. However, the present inventors have found that in a process according to the present invention, higher temperatures, e.g., about 190 and above, or about 200 and above, or about 210 and above, or about 220 and above or about 225° C. and above, up to about 240, or about 250, or about 260, or about 270, or about 280, or about 290° C., or sometimes even higher, can have one or more of the following advantages: lower branching index, lower selectivities to heavies (e.g., C15+), catalyst stability, lowered sensitivity to sulfur and oxygen containing impurities in the feedstream. The higher production of steam is also advantageous in refineries and chemical plants where steam is integrated throughout the facility.

Without wishing to be bound by theory, the improved performance is believed to be caused by the increased solvency and decreased reactivity of the feedstock composition of the invention. Pre-reacting monomer (here propylene) to dimer (here hexenes) and trimer (here nonenes) releases heat. The denser feedstock has a higher heat capacity and reduced propylene content reduces reaction rates. As a result, industrial reactors running the feedstock composition according to the invention have lower peak temperatures (both in the bulk and in the catalyst pellets) and more isothermal temperature profiles, which is believed to be partially responsible for the observed selectivity improvement.

The invention has been described above with reference to numerous embodiments and specific examples. Many variations will suggest themselves to those skilled in this art in light of the above detailed description. All such obvious variations are within the full intended scope of the appended claims.

Trade names used herein are indicated by a ™ symbol or ® symbol, indicating that the names may be protected by certain trademark rights, e.g., they may be registered trademarks in various jurisdictions. All patents and patent applications, test procedures, and other documents cited herein are incorporated by reference to the extent such disclosure is not inconsistent with this invention and for all jurisdictions in which such incorporation is permitted. Furthermore, when numerical lower limits and numerical upper limits are listed herein, ranges from any lower limit to any upper limit are contemplated.

What is claimed is:

1. A process for upgrading light olefins to higher olefins comprising contacting a feed comprising 10-40 wt % propylene and 40-80 wt % of dimer and trimer of propylene, based on the amount of olefin in said feed, with an oligomerization catalyst comprising ZSM-57 under oligomerization conditions in at least one reactor and recovering a fraction comprising C9.

2. The process of claim 1, wherein said feedstock composition is controlled by least one of: (a) recycle of intermediate or final product; (b) staged injection of reactant; and (c) utilization of at least two catalysts differing in oligomerization selectivity.

3. The process of claim 1, wherein said conditions are effective to produce a single phase in said reactor, including a temperature of between about 150 and 320° C. and a pressure of about 35 barg to about 110 barg.

4. The process of claim 1, wherein said conditions include a pressure of from about 60 barg to about 90 barg and a temperature of from about 160° C. to about 270° C.

5. The process of claim 1, wherein said feed includes impurities of heteroatom-containing species selected from oxygen, sulfur, and mixture thereof, in the amount of from about 10 ppm to about 100 ppm, based on the level of each heteroatom impurity present.

6. The process of claim 1, wherein said catalyst comprises a catalyst selective for conversion a C3-C5 monomer unit and a dimer of said monomer unit to a trimer of said monomer.

7. The process of claim 6, wherein said catalyst is MFS.

8. The process of claim 1, wherein said reactor is a tubular reactor and wherein said catalyst is a stacked series of a first catalyst selective for conversion of a C3-C5 monomer unit to a dimer of said monomer unit, on a second catalyst selective for conversion a C3-C5 monomer unit and a dimer of said monomer unit to a trimer of said monomer, wherein first catalyst is closest to the inlet and said second catalyst is closest to the outlet of said tubular reactor.

9. The process of claim 8, wherein said first catalyst is TON, and said second catalyst is MFS.

10. The process of claim 1, wherein said reactor is a chamber reactor comprising a series of at least two catalyst beds, a first catalyst bed consisting essentially of a first catalyst selective for conversion of a C3-C5 monomer unit to a dimer of said monomer unit, and a second catalyst bed selective for conversion a C3-C5 monomer unit and a dimer of said monomer unit to a trimer of said monomer.

11. The process of claim 10, wherein said first catalyst is TON, and said second catalyst is MFS.

12. The process of claim 1, wherein said feed further comprises butenes in the amount of about 0.5 wt % to about 20 wt %, based on the amount of olefin in said feed.

13. The process of claim 12, wherein said process further comprises a step of recovering a product comprising hexenes and heptenes, then separating said product into a first stream comprising predominantly hexene and a second stream comprising predominantly heptene, and recycling said second stream to a process comprising contacting a feedstream comprising propylene and said second stream with a dimerization catalyst under conditions sufficient to produce decene.

14. The process of claim 1, wherein said feed comprises butene isomers.

15. The process of claim 1, wherein said process further comprises a step of recovering a product comprising predominately hexenes and heptenes, separating said product into a first stream comprising predominantly hexene isomers and second stream comprising predominately heptene isomers, recycling said second stream to a process comprising contacting a feedsteam comprising butene and said hexene isomers with a dimerization catalyst under conditions sufficient to product decene and recycling said second stream to a process comprising contacting a feedstream comprising butene and said heptene isomer with a dimersization catalyst under conditions sufficient to produce undecene.

* * * * *